(12) United States Patent
Seguin

(10) Patent No.: US 6,461,366 B1
(45) Date of Patent: Oct. 8, 2002

(54) SURGICAL DEVICE FOR CONNECTING SOFT TISSUE

(75) Inventor: Jacques Seguin, Paris (FR)

(73) Assignee: Evalve, Inc., Redwood City, CA (US)

( * ) Notice: Subject to any disclaimer, the term of this patent is extended or adjusted under 35 U.S.C. 154(b) by 0 days.

(21) Appl. No.: 09/523,018

(22) Filed: Mar. 10, 2000

Related U.S. Application Data

(63) Continuation of application No. PCT/FR98/01960, filed on Sep. 12, 1997.

(51) Int. Cl.$^7$ ................................................ A61B 17/04
(52) U.S. Cl. ........................................ 606/144; 606/139
(58) Field of Search ................................ 606/139, 151, 606/157, 158, 148, 144, 143, 185

(56) References Cited

U.S. PATENT DOCUMENTS

| | | | |
|---|---|---|---|
| 2,108,206 A | | 2/1938 | Meeker |
| 4,297,749 A | | 11/1981 | Davis et al. |
| 4,809,695 A | | 3/1989 | Gwathmey et al. |
| 5,049,153 A | | 9/1991 | Nakao et al. |
| 5,069,679 A | * | 12/1991 | Taheri ........................ 606/139 |
| 5,403,326 A | | 4/1995 | Harrison et al. |
| 5,450,860 A | * | 9/1995 | O'Connor .................. 128/898 |
| 5,542,949 A | | 8/1996 | Yoon |
| 5,571,137 A | | 11/1996 | Marlow et al. |
| 5,571,215 A | | 11/1996 | Sterman et al. |
| 5,836,955 A | | 11/1998 | Buelna et al. |
| 5,954,732 A | | 9/1999 | Hart et al. |
| 5,980,455 A | | 11/1999 | Daniel et al. |
| 6,117,144 A | | 9/2000 | Nobles et al. |
| 6,269,819 B1 | | 8/2001 | Oz et al. |

FOREIGN PATENT DOCUMENTS

| | | |
|---|---|---|
| DE | 3504292 | 2/1985 |
| EP | 0179562 | 7/1989 |
| EP | 0558031 | 2/1993 |
| GB | 1598111 | 9/1981 |
| GB | 2151142 | 11/1984 |
| WO | WO 81/00668 | 3/1981 |
| WO | WO 92/12690 | 8/1992 |
| WO | WO 94/18893 | 9/1994 |
| WO | WO 98/07375 | 2/1998 |
| WO | WO 01/28432 A1 | 9/2000 |
| WO | WO 01/26557 A1 | 4/2001 |
| WO | WO 01/26557 A1 | 4/2001 |
| WO | WO 01/28432 A1 | 4/2001 |

* cited by examiner

*Primary Examiner*—Kevin T. Truong
(74) *Attorney, Agent, or Firm*—Townsend and Townsend and Crew LLP

(57) ABSTRACT

The invention comprises a surgical instrument including an external tube (2) and two elongated members (4) positioned in said tube (2), each of which includes a distal end (10a) for capturing one of the two tissue zones (M1,M2) to be attached. The instrument (1) may further comprise a catching member (22, 25) for each tissue (M1, M2) to be attached; a rod (15, 16) linked to each catching member (22, 25) enabling tension to move axially, said rod (15, 16) being separable from said catching member (22, 25) when a tension is exerted on it beyond a certain threshold; and a member (17a) forming a stop for locking axially each catching member (22, 25) during said tension.

23 Claims, 4 Drawing Sheets

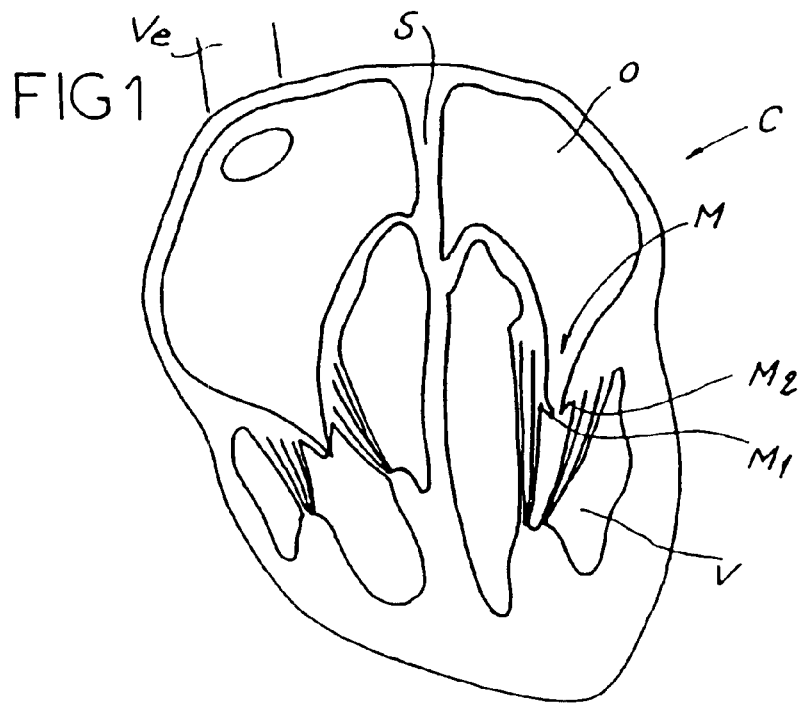
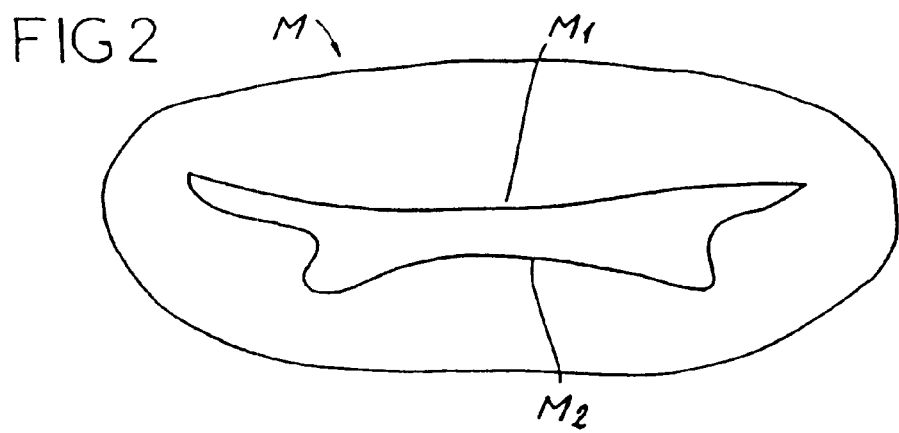
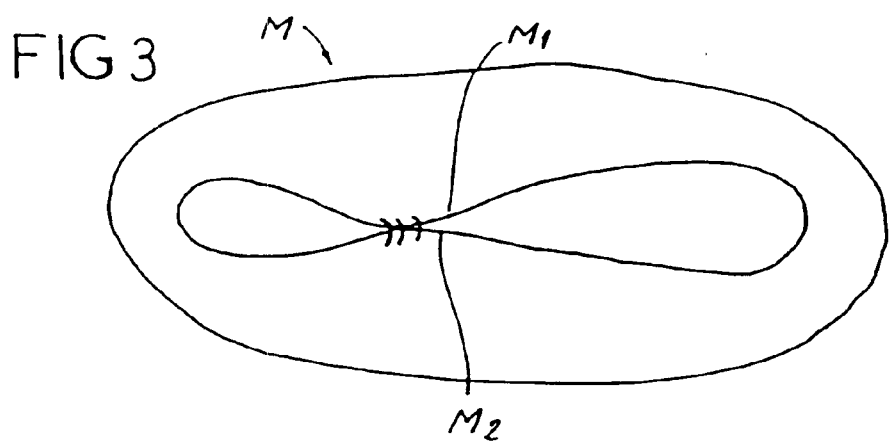

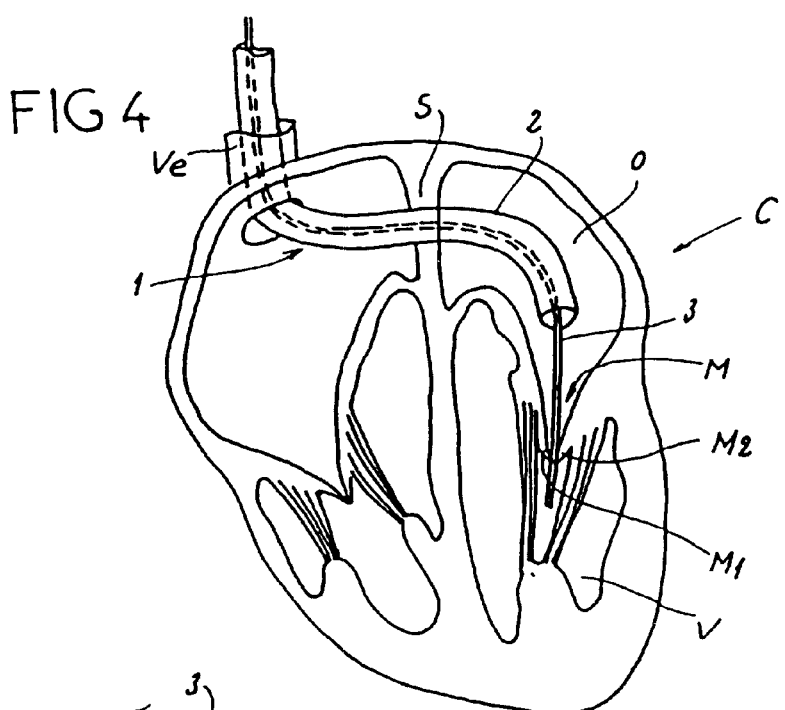
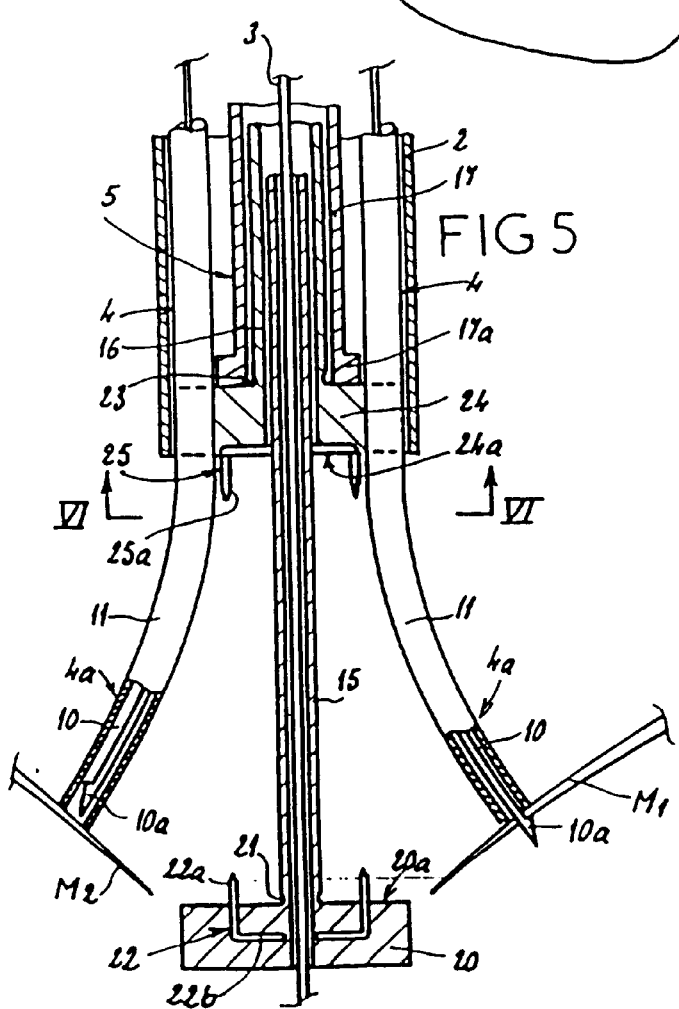
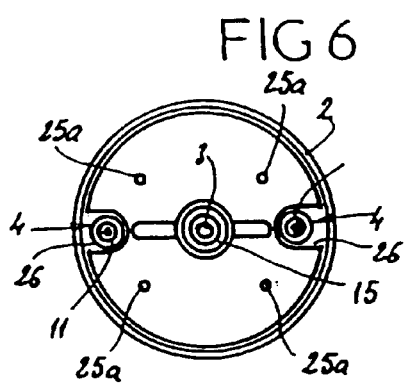

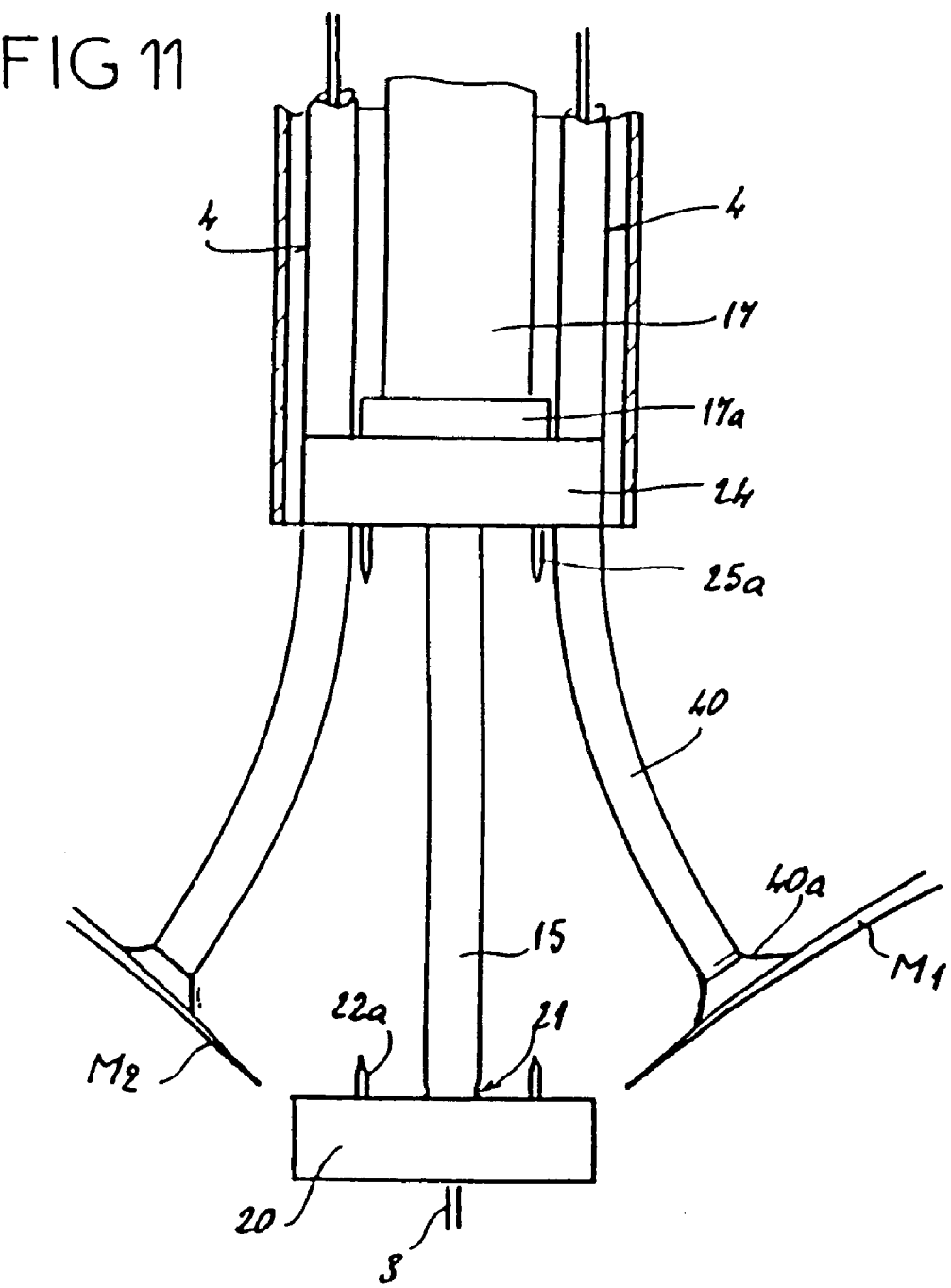

SURGICAL DEVICE FOR CONNECTING SOFT TISSUE

CROSS-REFERENCES TO RELATED APPLICATIONS

This application is a continuation of PCT/FR98/01960, which designates the United States, filed Sep. 12, 1997, the full disclosure of which is incorporated herein by reference.

BACKGROUND OF THE INVENTION

This invention provides a surgical device allowing the percutaneous connection of two soft tissue areas that are ordinarily separate. This device is particularly intended for reconstruction of heart valves, especially the mitral valve, and for the treatment of any malformation of a heart septum.

In a condition known as mitral insufficiency, the mitral valve does not completely shut, and does not prevent the back-flow of blood to the left atrium from the left ventricle. Surgical repair is then necessary. In a current procedure, a sternotomy is performed. The patient is then placed under extra-corporal blood circulation while the heart is stopped, and the heart chambers are opened to gain access to the mitral valve, usually through the left atrium. Once the mitral valve is accessed, repair procedures include annuloplasty and, more recently, suturing of the free edge of the anterior leaflet to the free edge of the back leaflet where the mitral insufficiency occurs.

These procedures are complicated and require general anesthesia, sternotomy and extra-corporal blood circulation. They also require high doses of anticoagulant therapy adding to the operative risk of a myocardial infarction and hemorrhage.

SUMMARY OF THE INVENTION

The methods of the present invention are performed percutaneously, diminishing considerably these risks. A surgical device allows the connection of two zones of soft tissue that are usually separate. In a particular embodiment, a connection is formed between a free edge area of an anterior mitral leaflet and a free edge area of a back mitral leaflet. Suitable surgical devices for performing tissue connection are described for example in EP 558 031 and WO 94/18893, and may comprise:

(a) a tube which may be inserted percutaneously until its distal extremity reaches the area around the tissues to be connected; and (b) two elongated elements inside that tube, each of which comprises a distal extremity having a device that grasps one of the two tissues to be connected;

(c) wherein the distal extremities of these elongated elements may be opened and closed in order to permit introduction into the desired area, allow the procedure.

Particular devices according to the present invention may further comprise:

(a) a grasping element, optionally having two parts for capturing each of the tissues to be connected, wherein the grasping or hooking element effects the connection of the two zones of tissue when brought close thereto by shifting of the, portions of distal extremities to a position where they meet;

(b) a rod connected to each of the grasping or hooking elements and operated from the proximal end of the tube in order to axially shift the elongated element, wherein the rod can be separated from the grasping or hooking element upon pulling beyond a given threshold; and (c) a wedge inside the tube, allowing the axial immobilization of each grasping or hooking element while pulling on them.

The rod positions the insertion of the hooking element up to the level of the tissue edges to be connected. The rod also engages the hooking element against the wedge in order to open the two hooking parts.

According to the present invention, the device may be used to remotely grasp through a percutaneous passage, to draw together, and to connect the two zones of tissue by a simple external manipulation.

Preferably, the tube, the elongated elements, and the rod are flexible enough to be inserted percutaneously and through a patient's vasculature for the treatment of the leaflets of a cardiac valve, in particular the mitral valve. Each of the elongated elements is made out of an elastically flexible material, and one of these elongated elements diverges from the longitudinal axis of the other. The two elongated elements can move axially in relation to the tube between (a) a retracted position within the tube where the ends of the elongated elements are flexibly bent and closed together, and (b) a position where the ends of the elongated elements spring open and diverge from each other in a way that permits those ends to capture the soft tissues in order to grasp them.

The elongated elements may be deployed to allow their distal extremities to grasp the tissue areas or may be retracted in order to make the insertion, shifting or 32 removal of the apparatus easier. Each elongated element may comprise a rod made of elastic material, with a curved distal extremity and/or a harpoon shape, and a sheath able to slide axially in a forward position to cover the distal extremity and slide back to uncover it.

According to a variation, each elongated element can be composed of a tube linked to a system that contracts its internal volume in order to grasp the corresponding tissue area, and expands to release the tissue with no lesion. In this case, the wide-mouthed shape of the elongated element's distal extremity will insure a large enough grasping surface.

Preferably, the device includes two hooking elements. One is operated on the distal side of the tissues, and the other, to be operated on the proximal side of the tissues, is situated between the first hooking element and the wedge element. This way the two hooking elements can be operated on both sides of the tissues and can be pressed together for a perfect attachment of those tissues.

BRIEF DESCRIPTION OF THE DRAWINGS

For greater clarity, the invention is described again in reference to the enclosed Figures representing two unrestricted examples of the invention in its optimal capacity.

FIG. 1 shows a longitudinal section of a heart with a mitral valve that does not shut properly and has to be treated with this device.

FIG. 2 shows the mitral valve before treatment.

FIG. 3 shows a mitral valve similar to FIG. 2 after treatment by suture according to the usual procedure.

FIG. 4 is a view similar to that of FIG. 1, with the device of the present invention inserted into a heart.

FIG. 5 is an enlarged view of a longitudinal section of the distal extremity of the device.

FIG. 6 shows a view of this distal extremity according to the line VI—VI of FIG. 5.

FIG. 11 illustrates an alternative embodiment of the device of the present invention.

DESCRIPTION OF THE SPECIFIC EMBODIMENTS

Figure 7:
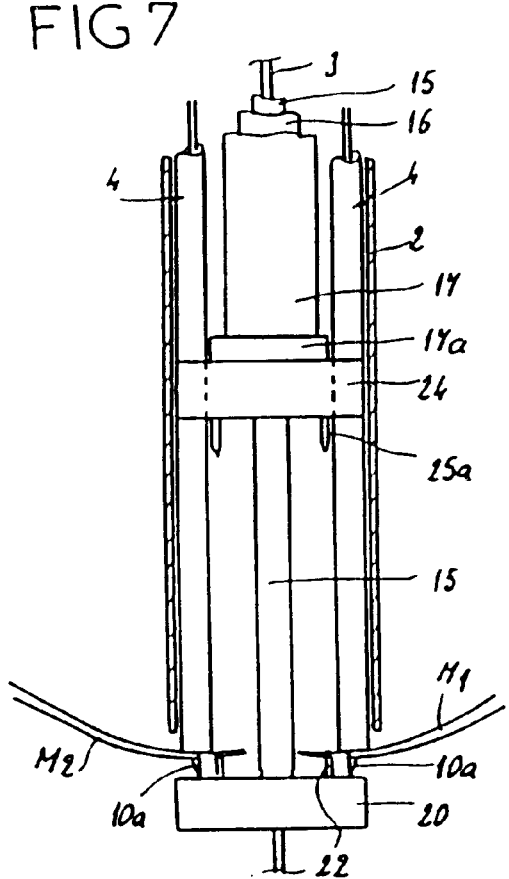
FIG. 7 and FIG. 8 are similar views to FIG. 5 at different stages of the procedure.

FIG. 1 shows a heart C with a mitral valve M having poorly opposed leaflets (M1, M2). Thus, the valve M does not shut tightly and no longer performs its back-flow function between the left atrium O and the left ventricle V. According to conventional procedures, after sternotomy, the patient is placed under extra-corporal blood circulation. The heart is stopped and the heart chambers are opened to directly reach to the valve M and stitch together the free opposite edges of both leaflets (M1, M2) as shown on FIGS. 2 and 3. Connecting leaflets M1 to M2 restores a good attachment between them and restores the imperviousness of valve M.

FIGS. 4 to 5 show a device (1) according to the present invention which enables the percutaneous connection of leaflet M1 to leaflet M2. This device (1) comprises an external tube (2), guidewire (3), two elongated elements (4), and a clipping system (5). The apparatus is sufficiently flexible to be percutaneously inserted into the heart C, through the patient's vascular, e.g., the Vena Cava Ve and the intra-atrial septum S. Guidewire (3) is inserted through valve M and so the distal extremity of external tube (2) is located in the left atrium O, with its distal opening facing mitral valve M.

Figure 8:
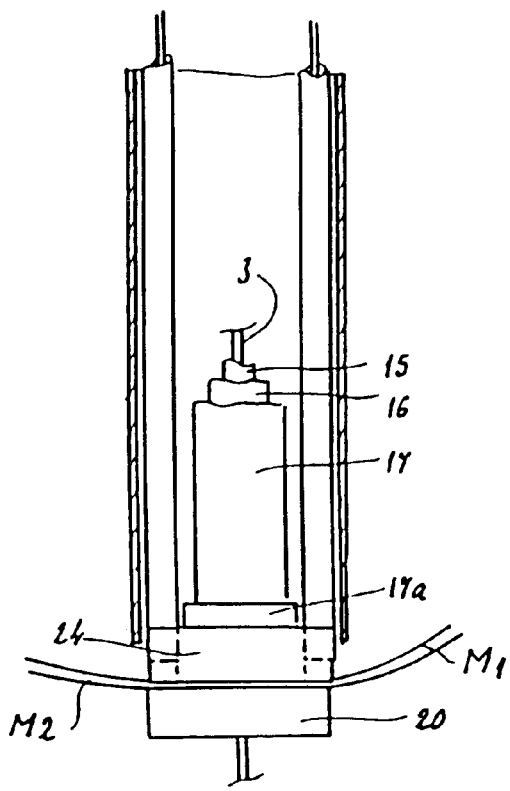

Each of the elongated elements (4) has a distal extremity (4*a*) that is normally curved to diverge outwardly. A rod (10) is made out of a relatively rigid but still elastic material, more particularly in metal, with a sheath (11) of synthetic material. The distal extremity (10*a*) of the rod (10) is sharp and more or less harpoon-shaped. The sheath (11) fits on the rod (10) and can slide axially to a forward position (as shown on left side of FIG. 5) in order to cover the distal extremity of the rod, and can slide back (as shown on the right side of FIG. 5) in order to uncover that same distal extremity (10*a*). The elongated elements (4) extend from the end of the tube (2). Because of this, they can be shifted axially in relation to the tube (2) between a retracted position where the extremities (10*a*) close together (FIG. 7 and 8) and an extended position where these same extremities (l0*a*) diverge from each other (FIG. 5). The clipping system (5) comprises three concentric tubular rods (15, 16, 17) that can be slidably introduced over the guidewire (3). Each rod can also slide axially in relation to the others. The internal rod (15) is linked to a disk (20) through a frangible area (21). The rod and disk (15 and 20) are made of molded synthetic material. The disk (20) is axially pierced in order to let the guidewire (3) pass through, and carries a clip (22). Side prongs (22*a*) of that clip extend from the proximal face (20*a*) of the disk (20). A central portion (22*b*) of the clip (22) having a central ring for receiving the guidewire (3) is embedded into the material of the disk (24).

The intermediate rod (16) is also connected by a frangible area (23) to a disk (24) with two clips (25). Side prongs (25*a*) of these clips extend from the distal face (24*a*) of this disk (24), and central portions of the prongs are embedded into the material of the disk (24). On each side, the disk (24) has two diametrically opposed notches (26, FIG. 6) to allow the passage of the elongated elements (4). The external rod (17) has an expanded distal extremity (17*a*) which engages the proximal face of the disk (24). Each of these rods (15, 16, 17) can be extended beyond the proximal extremity of tube (2) so they can be shifted by the operator.

A handle or other structure for manipulating the rods (15, 16, 17) will usually be provided at a proximal end of the device. The handle will permit deployment rod (15) while rod (17) is held in a desired position in relation to tube (2), and then deployment rod (16), while rod (17) is also held in the desired position in relation to tube (2).

In practice, under X-ray or echography control, the guidewire (3) is first inserted through Vena Cava Ve, the intra-atrial septum S, and mitral valve M. Then tube (2) and its internal parts are inserted into the Vena Cava Ve and through the septum S until the distal extremity of tube (2) is directed at mitral valve M (FIG. 4). At this stage, disk (20) should be held at the opening of tube 2 (FIG. 5), while elongate elements (4) are retracted so that their distal extremities are retracted into slots (26).

When the distal extremity of tube (2) is in the proper position, rod (15) is shifted to advance disk (20) beyond leaflets M1 and M2 and into the left ventricle V. Elongate elements (4) are then advanced to their extended positions, as shown in FIG. 5. As the elongate elements (4) are advanced, their distal extremities diverge. After the elements (4) are advanced, distal extremities (10*a*) of rods (10) are positioned close to leaflets (M1, M2). The sheaths (11) of elements (4) are then retracted in relation to the rods (10) in order to uncover the extremities (10*a*), each of which can then pierce and capture the adjacent leaflet M1 or M2. Tube (2) is then advanced over the elongate elements (4), drawing the distal extremities (4*a*) closer, as shown on FIG. 7. This action draws the free edges of leaflets M1 and M2 together.

Figure 9:
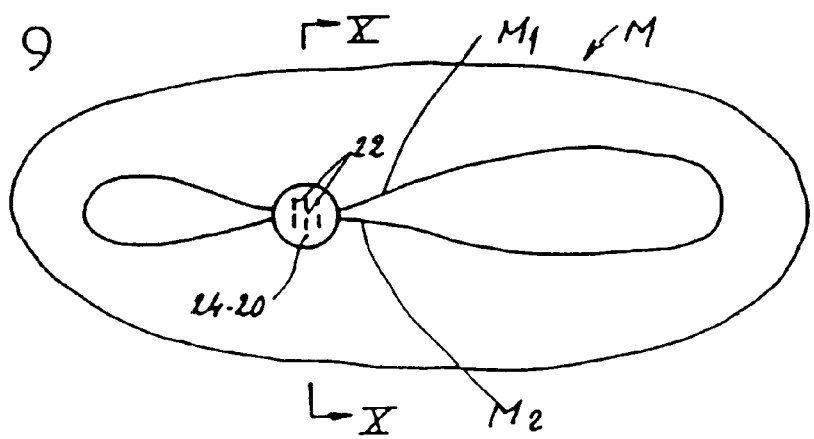
FIG. 9 is a similar view to FIG. 2 of the mitral valve after treatment with the device.
Figure 10:
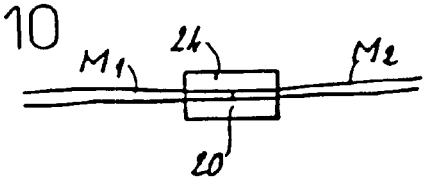
FIG. 10 is a view of this valve according to line X—X of FIG. 9.

Rod (17) is advanced distally in relation to tube (2), and rod (15) is pulled proximally in relation to tube (2) in order to insert the prongs (22*a* and 25*a*) of clips (22 and 25) into the leaflets M1 and M2. The tension on rod (15) forces the prongs (22*a* and 25*a*) against the opposed walls (20*a,* 24*a*) of the disks (20, 24) and breaks frangible area (21). This break gives the prongs of the clips enough freedom of movement to ensure a good connection between leaflets M1 and M2. The sheaths (11) are then advanced distally in relation to the rods (10) to engage leaflets (M1, M2). This facilitates the extremities (10*a*) of the rods from the leaflets (M1, M2). Rod (16) is then pulled while holding rod (17) in position to break frangible area (25). Leaflets (M1, M2) have thus been clipped to each other by their free edges, as shown in FIG. 9 and 10.

FIG. 11 shows a variation of the apparatus where rods (10) and sheaths (11) have been replaced by two catheters (40) having trumpeted distal extremities (40*a*). These catheters (40) project beyond the proximal end of tube (2) and may be attached to syringes that permit the creation of negative pressure. The grasping or releasing of leaflets (M1, M2) is then achieved by controlling the internal pressure within catheters (40). The trumpeted ends (40*a*) ensure a sufficient grip on leaflets (M1, M2). Those ends (40*a*) are preferably sufficiently flexible enough to bend slightly when they are drawn between the wall of tube (2) and two lateral slots (26) of disk (20). The other parts of this alternative device are the same as already described and bear the same record numbers.

It goes without saying that the invention is not limited to the above example and is opened to different variations. For instance, the unstressed shape of the extremities (10*a*) that hook the tissues could be of a curved J which is straightened when drawn into the sheaths (11). The elongated parts (4) and the connecting system could also be placed in separate tubes. The device (1) could be inserted arterially as well as veinously.

What is claimed is:

1. A method for percutaneously attaching valve leaflets, said method comprising:

percutaneously introducing a device through a patient's vasculature into a heart chamber;

capturing a first valve leaflet;

capturing a second valve leaflet separately from the first valve leaflet;

drawing the first and second captured leaflets together; and attaching the first valve leaflet to the second valve leaflet.

2. A method as in claim 1, wherein the valve leaflets are mitral valve leaflets.

3. A method as in claim 2, wherein percutaneously introducing the devices comprises advancing the device through the vena cava, through the intra-atrial septum, and into the left atrium above the mitral valve.

4. A method as in claim 3, wherein capturing the first valve leaflet comprises advancing a first elongate member from the device and securing the first leaflet to the first elongate member.

5. A method as in claim 4, wherein securing comprises piercing the leaflet with a harpoon-shaped tip.

6. A method as in claim 4, wherein securing comprises applying a vacuum to the leaflet.

7. A method as in claim 4, wherein capturing the second valve leaflet comprises advancing a second elongate member from the device and securing the second leaflet to the second elongate member.

8. A method as in claim 7, wherein securing comprises piercing the leaflet with a harpoon-shaped tip.

9. A method as in claim 7, wherein securing comprises applying a vacuum to the leaflet.

10. A method as in claim 7, wherein drawing the first and second valve leaflets together comprises drawing the first and second elongate members together.

11. A method as in claim 10, wherein the first and second elongate members diverge from each other when released from a covering sheath, wherein drawing said elongate members together comprises advancing the sheath over the elongate members.

12. A method as in claim 1, wherein attaching the free edges of the leaflets comprises clipping the leaflets together.

13. A method for percutaneously attaching valve leaflets, said method comprising:

percutaneously introducing a device through a patient's vasculature into a heart chamber; said device carrying a clipping system including first and second elements;

drawings the first element upwardly to engage the leaflets from below;

positioning the second element over the leaflets to capture said leaflets between said members; and leaving the elements in the heart to hold the leaflets together.

14. A method as in claim 13, further comprising detaching the elements from the device and withdrawing the device from the heart.

15. A method as in claim 13, wherein the first and second elements are positioned near a center of an opening between the valve leaflets.

16. A method as in claim 13, wherein the device further carries a first elongate element and a second elongate element, wherein the method further comprises:

capturing a first valve leaflet with the first elongate element;

capturing a second valve leaflet separately from the first valve leaflet with the second elongate element; and drawing the first and second captured leaflets together prior to capturing the leaflets between the first and second elements.

17. A method as in claim 16, wherein capturing the first leaflet comprises piercing the leaflet with a harpoon-shaped tip.

18. A method as in claim 16, wherein capturing the first leaflets comprises applying a vacuum to the leaflet.

19. A method as in claim 16, wherein capturing the second valve leaflet comprises advancing a second elongate member from the device and securing the second leaflet to the second elongate member.

20. A method as in claim 19, wherein capturing the second leaflet comprises piercing the leaflet with a harpoon-shaped tip.

21. A method as in claim 19, wherein capturing the second leaflet comprises applying a vacuum to the leaflet.

22. A method as in claim 13, wherein the valve leaflets are mitral valve leaflets.

23. A method as in claim 22, wherein percutaneously introducing the devices comprises advancing the device through the vena cava, through the intra-atrial septum, and into the left atrium above the mitral valve.

* * * * *